US00PP30555P2

(12) United States Plant Patent
Hansen

(10) Patent No.: US PP30,555 P2
(45) Date of Patent: Jun. 4, 2019

(54) ***CLEMATIS* PLANT NAMED 'VIOLET STARDUST'**

(50) Latin Name: ***Clematis integrifolia* X *recta* hybrid**
Varietal Denomination: Violet Stardust

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 15/932,903

(22) Filed: May 17, 2018

(51) Int. Cl.
*A01H 5/02* (2018.01)
*A01H 6/72* (2018.01)

(52) U.S. Cl.
USPC ..... Plt./228

(58) Field of Classification Search
USPC ..... Plt./228
See application file for complete search history.

*Primary Examiner* — Susan McCormick Ewoldt

(57) ABSTRACT

The new hybrid plant of *Clematis* 'Violet Stardust' with ovate to oddly compound foliage having a greyed-purplish blush when young, violet-blue, lanceolate, recurved tepals on upright to outwardly facing flowers beginning late spring and reblooming into late summer on non-vining stems that can be either used as a ground cover, staked or allowed the support of other nearby plants.

2 Drawing Sheets

Botanical denomination: *Clematis integrifolia* X *recta* hybrid.

Cultivar designation: 'Violet Stardust'.

BACKGROUND OF THE INVENTION

The present invention relates to a new and distinct plant of bush-type *clematis*. The new plant was hybridized by the inventor at a wholesale perennial nursery in Zeeland, Mich., USA. 'Violet Stardust' was a single seedling selection from a cross made in the summer of 2012. The seed was from an unreleased, unnamed, blue-flowering selection of *Clematis integrifolia* (not patented) as the female parent, times *Clematis recta* 'Serious Black' (not patented) as the male parent. The new plant passed the original evaluation in summer of 2014 at a wholesale perennial nursery in Zeeland, Mich., USA and was the subject of the subsequent evaluations identified by the breeder code 12-6-2. The new plant was selected from among one other seedling from the above cross and hundreds of other *Clematis* seedling from other crosses growing at the same nursery in Zeeland, Mich. which met the rigorous criteria of excellent foliage and habit established as breeding goals.

'Violet Stardust' has been asexually propagated since 2014 by shoot tip cuttings at the same nursery in Zeeland, Mich. The resultant asexually propagated plants have remained stable and exhibit the identical characteristics as the original plant.

No plants of *Clematis* 'Violet Stardust' have been disclosed or sold, under this or any name, in this country or anywhere in the world, prior to the filing of this application, with the exception of that which may have been disclosed within one year of the filing of this application and was either derived directly or indirectly from the inventor.

BRIEF SUMMARY OF THE INVENTION

'Violet Stardust' differs from all other *clematis* known to the applicant. The nearest known cultivar is 'Pretty in Blue'

U.S. Plant Pat. No. 14,823. 'Pretty in Blue' has flowers that are slightly larger than the new plant and without the greyed-purple blushing on stems and younger foliage. The male parent is taller, with smaller near-white flower petals and reddish purple foliage in the spring. The female parent is shorter than the new plant and has longer tepals with more bluish hue. The female parent has larger, ovate, simple foliage.

The new plant, 'Violet Stardust', differs from all *clematis* known to the inventor in the following combined traits:

1. The foliage is ovate proximally and oddly compound to rarely lobed in distal region of the stem, and young foliage is blushed greyed purple.
2. Drooping solitary flowers begin in late spring with rebloom into the late summer typically having four, or rarely five, lanceolate tepals per flower.
3. Reflexed violet-blue tepals are slightly shiny on adaxial surface.
4. Plant habit is non-vining and can be used as a ground cover, staked or allowed the support of other nearby plants.

BRIEF DESCRIPTION OF THE DRAWINGS

The photographs of the new plant demonstrate the overall appearance of trial garden at a wholesale perennial nursery in Zeeland, Mich., USA. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
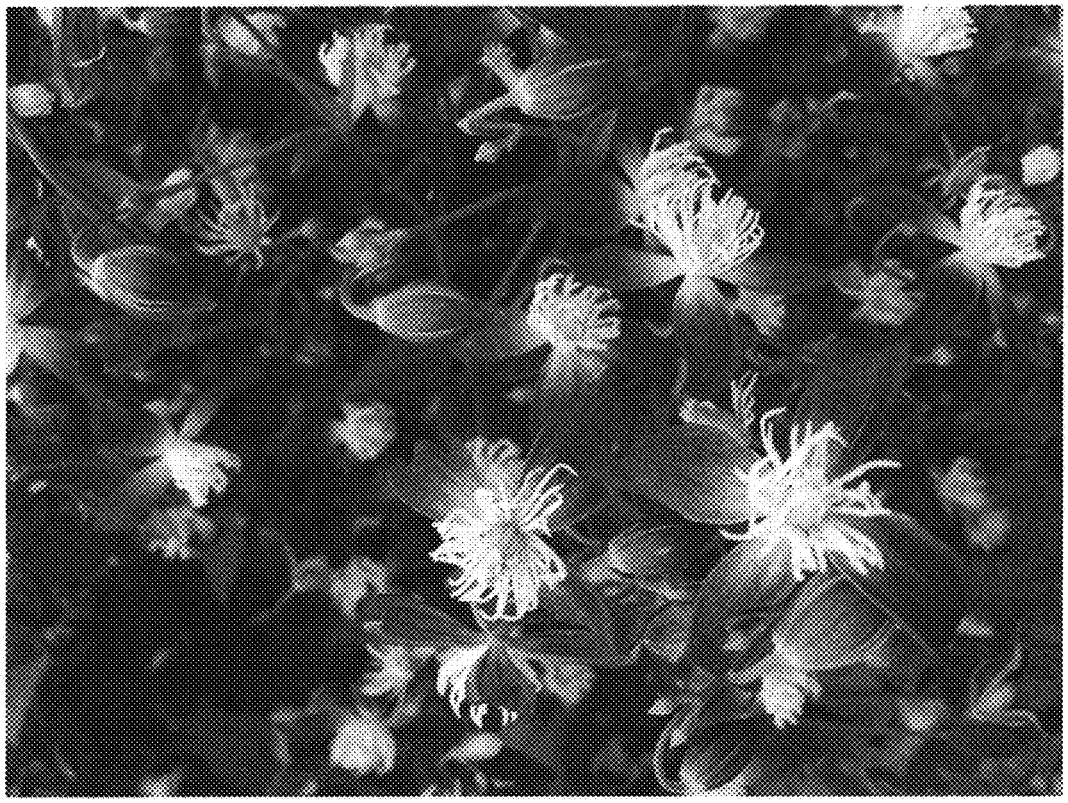
FIG. 1 a close-up of a flower and bud on a five-year-old plant.
Figure 2:
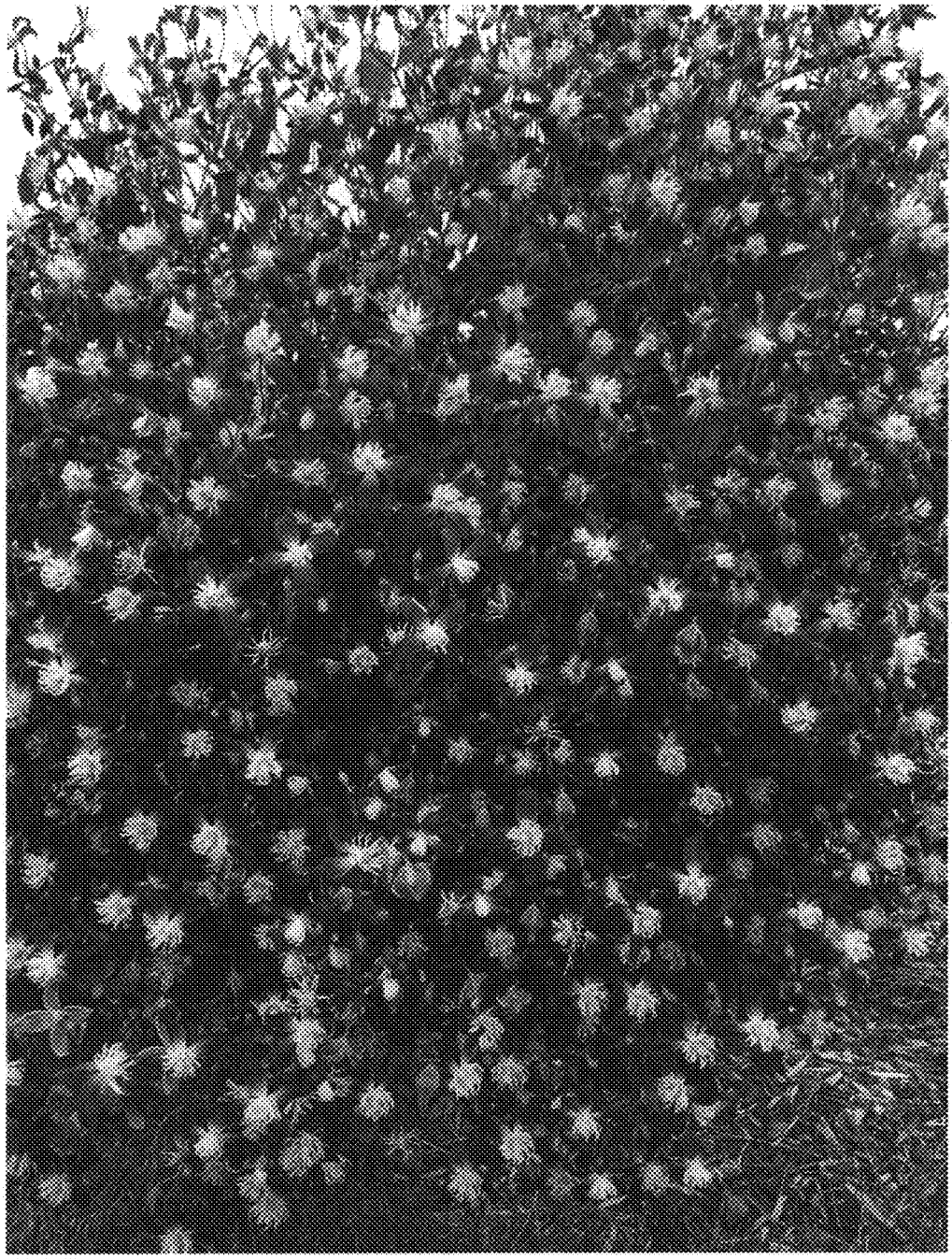
FIG. 2 shows the flowers and flower density of a staked five-year-old plant early in the flowering season.

The following description is based on a five-year-old plant growing in a full-sun trial garden with supplemental water and fertilizer at a wholesale perennial nursery in Zeeland, Mich., USA. The new plant has not been grown under all possible environments and may phenotypically appear different under different conditions such as light, temperatures, fertilizer, and water, without any difference in genotype. The color descriptions are from the 2015 edition of The Royal Horticultural Society Colour Chart except where common dictionary terms are used.

Parentage: The female (seed parent) an unnamed blue-flowering selection of *Clematis integrifolia*; the male (pollen parent) was *Clematis recta* 'Serious Black';

Plant habit: Winter-hardy, non-vining, herbaceous perennial of compact stems producing upright habit, dying to the ground each winter; to about 64.0 cm tall in flower and 70.0 cm across if not supported;

Roots: Coarse, branched; tan to light brown in color depending on soil type;

Growth rate: Rapid, finishing in four-liter container in about 8 to 10 weeks from a one-year-old vernalized plant;

Stems: Ribbed in cross-section, six-sided with carina; glabrous proximally and pubescent distally; slightly branched; becoming hollow in center; about 80 per plant; to about 40.0 cm long and 5.0 mm diameter at base;

Stem color: Proximally between RHS N167C and RHS N167D, distally nearest RHS 146B with carina nearest RHS N186C;

Internode: Average about 6.5 cm apart and 8.0 mm across;

Internode color: Variable, between RHS 145D and RHS 144D;

Foliage: Deciduous; opposite; simple, to compound, rarely lobed; ovate (proximally) to oddly compound pinnate with five leaflets (distally); apex acute; base rounded to attenuate on simple leaves and oblique on compound leaflets; margin entire, ciliolate; minutely puberulent abaxial and glabrous adaxial;

Leaf blade size: Simple leaves to about 8.0 cm long and about 4.0 cm wide in middle; pinnate leaves to about 11.5 cm long and about 5.5 cm wide distally, terminal leaflet to about 5.5 cm long and about 2.2 cm wide, proximal leaflets about 6.5 cm long and about 2.5 cm wide;

Leaf and leaflet color: Proximal mature leaves adaxial surface nearest RHS 137A, abaxial surface nearest RHS 146B; young emerging leaves adaxial surface nearest RHS 136A with moderate to light blushing of nearest RHS 187A, abaxial surface between RHS 146A and RHS 146B with moderate blushing of nearest RHS 187A;

Foliar fragrance: None detected;

Petiole of simple leaves: Flattened to slightly concavo-convex; with ciliolate margin; glabrous adaxial, puberulent abaxial; partially clasping base; to about 18.0 mm long and 6.0 mm wide;

Petiole of compound leaves: Concavo-convex; with ciliolate margin; puberulent abaxial and adaxial; partially clasping base; to about 24.0 mm long and 3.5 mm wide at base;

Leaflet attachment to rachis: Sessile;

Rachis: To about 6.0 cm long and 1.5 mm wide; sparsely puberulent adaxial and abaxial; slightly flattened adaxial and rounded abaxial;

Rachis color: Variable; nearest RHS 146C to RHS N186C in regions of high light exposure;

Petiole color: Abaxial nearest RHS 146D, adaxial nearest RHS 146C; with blush in areas of high light exposure of nearest RHS N186C;

Veins: Palmate, multi-nerved; abaxial prominent and sparsely puberulent; adaxial slightly concave and very sparsely puberulent; convergent;

Vein color: Adaxial mature leaves and leaflets nearest RHS 146D; abaxial mature leaves nearest RHS 146C; adaxial young leaves nearest RHS 146C lightly blushed with nearest RHS N186C; abaxial young leaves nearest RHS 146C moderately blushed with N186C;

Inflorescence: Dichasial cyme;

Flower attitude: Buds upright, flowers upright to outwardly when mature;

Flower fragrance: Lightly sweet;

Flower period: Late spring with rebloom into late summer; individual flowers remaining effective in flower for about 6 to 8 days;

Peduncle: Terete; puberulent; to about 13.5 cm long and 2.0 mm in diameter, average 11.0 cm long and 1.5 mm diameter;

Peduncle attitude: Attitude upright;

Peduncle color: Variable, between RHS 147A and RHS 146C with faint blushing of RHS N186C distally where exposed to more light;

Buds one day prior to opening: Conical with narrowly acute apex, and rounded base; glabrous with carina long tepal unions and center veins tomentose; about 16.0 mm long and 8.0 mm diameter;

Bud color: Nearest RHS 83C with carina along tepal unions nearest RHS N82C;

Flower: Solitary; perfect; incomplete; campanulate, cruciform; actinomorphic; about 3.8 cm across and 2.5 cm deep;

Flower angle: Upright to slightly outwardly;

Tepals: Typically four; lanceolate; acute apex; cuneate to truncate base; recurved distally; tri-nerved with midrib and one pair of main veins; margins entire, becoming slightly revolute; glabrous abaxial and adaxial;

Tepal size: About 18.0 mm long and 7.0 mm wide in middle;

Tepal color: Adaxial center nearest RHS N87D, adaxial distally nearest RHS N87B; abaxial nearest RHS N87C;

Petals and sepals: Not present;

Androecium: About 60; flattened dorsa-ventrally, glabrous proximal half; total 9.0 mm long and 2.0 mm wide;

*Filaments*.—About 5.0 mm to 6.0 mm long; color nearest RHS NN155A.

*Anthers*.—Basifixed; longitudinal; ellipsoidal; toward external radius of flower; to about 3.0 mm long and 1.2 mm diameter, decreasing toward flower axis; color nearest RHS 11B.

*Pollen*.—Abundant; powdery; color nearest RHS 11C.

Gynoecium: About 40 internal to androecium; pilose with many hairs 5.0 to 6.0 mm long;

*Style*.—Terete; about 6.0 mm long and 0.2 mm diameter; pilose; color nearest RHS 155D.

*Stigma*.—Ellipsoidal; about 2.0 mm long and 0.5 mm diameter; color nearest RHS 155D.

*Receptacle*.—Semi-dome shaped; about 3.0 mm diameter across at base and 2.0 mm tall; color nearest RHS 160A.

*Fruit and seed*.—Not yet observed.

Culture: *Clematis* 'Violet Stardust' grows best in full sun with ample moisture, good drainage and mulch. The new plant is cold hardy from USDA zones 3 to at least zone 7.

Disease and pest tolerance: Pest and disease resistance and tolerance outside of that normal for *Clematis* is not known at this time.

It is claimed:

1. The new and distinct ornamental plant named *Clematis* 'Violet Stardust' as herein described and illustrated.

* * * * *